United States Patent
Hornauer et al.

(10) Patent No.: US 7,229,771 B2
(45) Date of Patent: Jun. 12, 2007

(54) POLYETHYLENE GLYCOL-DERIVATIZED BIOMOLECULES AND THEIR USE IN HETEROGENEOUS DETECTION METHODS

(75) Inventors: Hans Hornauer, Peissenberg (DE); Peter Sluka, Weilheim (DE); Johann Karl, Peissenberg (DE); Helmut Lenz, Tutzing (DE); Wolfgang Mutter, Bernried (DE)

(73) Assignee: Roche Diagnostics GmbH, Mannheim (DE)

( * ) Notice: Subject to any disclaimer, the term of this patent is extended or adjusted under 35 U.S.C. 154(b) by 0 days.

(21) Appl. No.: 09/184,043

(22) Filed: Nov. 2, 1998

(65) Prior Publication Data

US 2002/0052009 A1 May 2, 2002

(30) Foreign Application Priority Data

Nov. 3, 1997 (DE) ................ 197 48 489

(51) Int. Cl.
*G01N 33/53* (2006.01)
*G01N 33/543* (2006.01)
*G01N 33/545* (2006.01)
*G01N 33/547* (2006.01)
*C07K 1/10* (2006.01)

(52) U.S. Cl. ............... 435/7.1; 435/7.5; 435/7.92; 436/518; 436/531; 436/532; 530/402; 530/812

(58) Field of Classification Search ............ 435/7.5, 435/962, 7.1, 7.92; 436/531, 811, 815, 518, 436/532; 530/402, 812
See application file for complete search history.

(56) References Cited

U.S. PATENT DOCUMENTS 5,108,568 A * 4/1992 Van Alstine ............ 204/180.1
5,240,602 A * 8/1993 Hammen ................ 210/198.2
5,306,621 A * 4/1994 Kricka ..................... 435/7.91
5,512,492 A * 4/1996 Herron et al. ............. 436/518
5,516,703 A * 5/1996 Caldwell et al.
5,677,196 A * 10/1997 Herron et al. ............. 436/518
5,832,165 A * 11/1998 Reichert et al. ........... 385/130
5,871,649 A * 2/1999 Ofsthun et al. ............ 210/645
5,932,296 A * 8/1999 Sluka et al. ............... 427/491
6,015,897 A * 1/2000 Theodore et al. .......... 435/7.5
6,048,698 A * 4/2000 Eaton et al. ................ 435/6
6,284,503 B1 * 9/2001 Caldwell et al.

FOREIGN PATENT DOCUMENTS

| DE | 40 11 601 A1 | 10/1991 |
| DE | 40 04 296 A1 | 8/1994 |
| EP | 0 517 516 A1 | 12/1992 |
| EP | 0 516 749 B1 | 5/1994 |
| EP | 0 664 452 A | 7/1995 |
| EP | 0 664 452 A2 | 7/1995 |
| EP | 0 713 095 A | 5/1996 |
| EP | 0 713 095 A2 | 5/1996 |
| WO | WO 94/27137 | 11/1994 |
| WO | WO 94 27137 A | 11/1994 |

OTHER PUBLICATIONS

S. Zalipsky, Bioconjugate Chem., vol. 6, pp. 150-165, 1995.*
Derwent Publications Ltd., XP002193414, Abstract of JP 08 012699 A; Jan. 16, 1996.
Abstract of EP 0664452, Published Jul. 26, 1995.
Database WPI, Section Ch, Week 199612, Derwent Publications LTD., London GB; 5 AN 1996-112719 XP002193414 (JP 08 012699 Jan. 16, 1996).

* cited by examiner

*Primary Examiner*—Long V. Le
*Assistant Examiner*—Shafiqui Haq
(74) *Attorney, Agent, or Firm*—Rothwell, Figg, Ernst & Manbeck, P.C.

(57) ABSTRACT

The use of polyalkylene oxide modified reagents is disclosed in a method for the detection of an analyte or in suitable reagent kits for such methods.

15 Claims, No Drawings

POLYETHYLENE GLYCOL-DERIVATIZED BIOMOLECULES AND THEIR USE IN HETEROGENEOUS DETECTION METHODS

RELATED APPLICATIONS

This application claims foreign priority to GERMANY Application 19748489.1 filed Nov. 3, 1997.

The invention concerns methods for the detection of an analyte in a sample and suitable reagent kits for such methods.

Methods for the detection of an analyte in a sample in which a solid phase is used are called heterogeneous test formats. A problem in such methods is that components of the sample or of the test reagents often bind unspecifically to the solid phase which can lead to false test results. This unspecific binding is observed particularly frequently in samples from body fluids e.g. serum or plasma. In order to suppress this unspecific binding it is possible to add surface active substances, such as e.g. Tween 20, to the reagents (WO 88/07683). In addition it is known that metallic surfaces (Whitesides et al., Science 252 (1991), 1164-1166) and oxidic surfaces (EP-A-0 664 452) can be functionalized with reactive polyethylene glycol derivatives in order to minimize unspecific binding on the surface.

The surface active substances of the prior art used to reduce unspecific binding have the disadvantage that they displace molecules, such as solid phase receptors, bound to the solid phase and in this manner impair the test function. Furthermore, detergent surfactants produced on an industrial scale which have a heterogeneous composition and occasionally contain impurities are usually used as surface active substances. The resulting batch variations often lead to interferences and non-reproducible results. Moreover the structure of sensitive solid phase molecules such as proteins may be disturbed by the surface active substances and they may be ultimately denatured.

The functionalization of metallic or oxidic surfaces with polyethylene glycol known from the prior art is, on the one hand, limited to certain types of surfaces and, on the other hand, is not sufficient to prevent unspecific binding to a layer of biomolecules applied to a solid phase surface.

Hence the object of the present invention was to provide a new method for reducing unspecific binding to a solid phase when an analyte is detected in a sample in which it is possible to at least partially avoid the disadvantages of the prior art.

A first aspect of the present invention concerns a method for the detection of an analyte in a sample comprising the steps:

(a) preparing a solid phase comprising, in an immobilized form, an analyte-specific solid phase reactant and an analyte-unspecific biomolecule which is coupled to a poly($C_2$-$C_3$)-alkylene oxide, (b) incubating the sample with the solid phase and a test reagent and (c) detecting the presence or/and the amount of the analyte in the sample.

Blocking the solid phase with a polyalkylene oxide, in particular with a polyethylene glycol-modified analyte-unspecific biomolecule, resulted in a considerable reduction of the unspecific binding of sample components to the solid phase without simultaneously significantly impairing the test sensitivity. The blocking reagent can be added during or/and after immobilization of the solid phase reactant. A solid phase which is pre-coated with an analyte-specific solid phase reactant is particularly preferably afterwards blocked with an analyte-unspecific biomolecule.

Good results were obtained by using solid phases which have "defined test" areas i.e. defined zones that are coated with a solid phase reactant which are spatially separated from other test areas by inert zones. Solid phases that are coated over the whole area with an analyte-unspecific pre-coating e.g. with streptavidin and which contain at least one spatially limited test area immobilized on the one analyte-specific solid phase reactant are particularly preferred. The defined test areas preferably have a diameter of 10 µm to 10 mm. Miniaturized test areas are particularly preferred with a diameter of 10 µm to 2 mm. Furthermore solid phases are preferred with several test areas which can contain different analyte-specific solid phase reactants and are also referred to as array systems (cf. e.g. U.S. Pat. Nos. 5,432,099; 5,516,635 and 5,126,276). These array systems enable several analyte determinations to be carried out simultaneously on one sample.

The solid phase in the method according to the invention comprises an arbitrary support, non-porous supports such as supports with a plastic, glass, metal or metal oxide surface being preferred. Porous supports such as test strips are also suitable.

An analyte-specific solid phase reactant i.e. a biomolecule which can specifically interact with an analyte to be determined or, in the case of competitive test formats, with an analogue of an analyte to be determined, is immobilized on the solid phase. Examples of analyte-specific solid phase reactants are antibodies, antigens, peptides, haptens, nucleic acids, nucleic acid analogues, glycoproteins, saccharides, lipoproteins and other biomolecules.

The solid phase reactant can be immobilized by known methods e.g. by direct adsorptive binding, by covalent coupling or preferably by coupling via high affinity binding pairs. For this the solid phase is firstly coated with a first partner of a high affinity binding pair and on this a conjugate of the solid phase reactant with the second partner of the binding pair is immobilized. Examples of suitable high affinity binding pairs are streptavidin or avidin/biotin or a biotin derivative (for example desthiobiotin, iminobiotin, aminobiotin or another substance capable of binding with high affinity to streptavidin or avidin), antibody/hapten (for example digoxigenin, fluorescein etc.), antibody/antigen (for example peptide or polypeptide), lectin/sugar and receptor/ligand (for example homone receptor/hormone). Streptavidin or avidin/biotin are particularly preferably used as the high affinity binding pair.

The method according to the invention preferably comprises blocking unspecific binding sites on the solid phase that is already coated with the analyte-specific solid phase reactant by incubation with an alkylene oxide-modified binding molecule which acts as a blocking substance. The duration and temperature of the incubation can be varied within wide ranges e.g. incubation temperatures of 4° C. to 40° C. and incubation times of 1 min to 1 h.

Suitable blocking substances are analyte-unspecific or inert biomolecules which are capable of binding to the solid phase and do not interfere with the detection method, for example proteins such as albumins, unspecific antibodies or fragments thereof, or polysaccharides such as dextrins etc. The blocking substance can be bound to the solid phase by means of adsorptive or covalent interactions. However, binding by means of high affinity binding pairs is preferred. In particular in the case of a solid phase which contains the solid phase reactants immobilized by means of a high affinity binding pair, a blocking substance is preferably used which comprises the second partner of the binding pair e.g. a biotinylated protein which contains one or several polyalkylene oxide residues. Alternatively the use of blocking substances is also preferred in which one or several polyalkylene oxide residues are directly coupled to the second partner of the binding pair.

Preferred blocking substances are conjugates of the general structural formulae (Ia) or (Ib):

$$P_r[-(AO_n)T]_m \quad (Ia)$$

$$P_r\text{-}I\text{-}[-(AO_n)T]_m \quad (Ib)$$

in which
P is a partner of a high affinity binding pair,
I is a biomolecule,
r is a number from 1 to 10,
AO is a $(C_2\text{-}C_3)$ alkylene oxide group,
n is a number from 5 to 500
T is an end group preferably selected from OH $C_1\text{-}C_4$ alkoxy and acyl and
m is a number from 1 to 10.

P is preferably a hapten, biotin or a biotin derivative. P is particularly preferably biotin or a biotin derivative. I is preferably a polypeptide or a saccharide. In conjugates of formula (Ia) r is preferably 1.

AO can be a $(C_2\text{-}C_3)$ alkylene oxide group i.e. an ethylene oxide or/and a propylene oxide group. AO is preferably an ethylene oxide group but combinations of ethylene oxide and propylene oxide groups are also suitable. n is preferably a number from 10 to 250 and particularly preferably 20 to 200.

T is an end group (including the terminal O atom of the polyoxyalkylene units), which is compatible with further test and sample components, i.e. which does not significantly enter undesired reactions. Preferably T is a hydroxy group, $C_1\text{-}C_4$ alkylether group, particularly methoxy, or a $C_1\text{-}C_4$ acyl group, e.g. an acetyl group. In conjugates of the structural formula (Ia) m is preferably 1.

The conjugates according to structural formula (Ia) and (Ib) are preferably used as blocking reagents in detection methods. After immobilization on a solid phase, they are preferably no longer able to bind with high affinity via the component P to dissolved biomolecules in the sample or in the test reagent.

A further subject matter of the invention is a solid phase with a coating which contains one or several conjugates (Ia) or/and (Ib) and preferably an analyte-specific solid phase reactant. The conjugates according to the invention can be used to reduce unspecific binding to a solid phase in a method for the detection of an analyte for example in an immunological or a nucleic acid hybridization method. A further subject matter of the first aspect of the present invention is a reagent kit for the detection of an analyte which contains a conjugate according to the invention or a solid phase according to the invention in addition to other test components.

In a particularly preferred embodiment biotin-polyethylene glycol compounds are used which are PEG chains which have been functionalized with a biotin residue at one chain end. The other chain end preferably carries a hydroxyl or a methoxy group. The biotin-PEG conjugates are applied to a steptavidin solid phase after or at the same time as a biotinylated analyte-specific solid phase reactant e.g. an antibody. The conjugate binds to the free biotin binding sites of the streptavidin solid phase that are still accessible. The non-bound biotin-PEG conjugate can be removed by washing. The resulting solid phase can be dried in this state without impairing the function. The unspecific binding of a surface treated with a conjugate according to the invention is greatly reduced compared to an untreated surface or compared to a surface treated with a non-alkylene-oxide-modified blocking substance. A further advantage is that the solid phase according to the invention can also be treated with the blocking conjugate and thus provided with the desired properties after application of the solid phase reactant. In solid phases which have defined test areas and a continuous pre-coating, a considerable reduction of unspecific binding is found within the test areas as well as outside these test areas (e.g. empty streptavidin solid phase). The ability of the solid phase to bind the analyte remains surprisingly uninfluenced.

A second aspect of the present invention is a method for the detection of an analyte in a sample comprising the steps:
(a) preparing a solid phase on which a solid phase reactant is immobilized using a modified solid phase reactant which is coupled to a poly($C_2\text{-}C_3$)-alkylene oxide,
(b) incubating the sample with the solid phase and a test reagent and
(c) detecting the presence or/and the amount of the analyte in the sample.

According to this second aspect of the invention a polyalkylene oxide modified solid phase reactant is immobilized on the solid phase. On the one hand, the modified solid phase reactant can be a universal solid phase reactant i.e. a reactant which cannot react specifically with the analyte but rather with a further solid phase reactant that is immobilized covalently, adsorptively or via a high affinity binding pair on the solid phase. Examples of universal solid phase reactants are for example streptavidin or anti-hapten antibodies which can react with a biotinylated or hapten-conjugated analyte-specific additional solid phase reactant. On the other hand or additionally the analyte-specific solid phase reactant can also be a polyalkylene oxide-modified solid phase reactant.

A universal modified solid phase reactant can for example be a partner of a high affinity binding pair or a conjugate of an analyte-unspecific biomolecule with a partner of a high affinity binding pair. Examples of universal solid phase reactants which are themselves the partner of a high affinity binding pair are polypeptides such as streptavidin, avidin, hapten-specific antibodies, lectins and polymeric conjugates thereof. On the other hand, it is also possible to use a conjugate of an analyte-unspecific biomolecule with a partner of a high affinity binding pair as a universal solid phase reactant, for example an inert polypeptide or polysaccharide coupled to biotin, biotin derivatives, haptens or sugars.

Even when using an analyte-specific modified solid phase reactant it is preferable that this is a conjugate with a partner of a high affinity binding pair. Examples of such analyte-specific modified solid phase receptors are analyte-specific antibodies, antigens, nucleic acids, nucleic acid analogues and lectins.

In one embodiment of the second aspect of the present invention conjugates of the general structural formula (II) are used:

$$F[-(AO_n)T]_m \quad (II)$$

in which
F is a polypeptide selected from lectins, streptavidin, avidin and antibodies,
r is a number from 1 to 10,
AO is a $C_2\text{-}C_3$-alkylene oxide group,
n is a number from 5 to 500,
T is an end group preferably selected from OH, $C_1\text{-}C_4$ alkoxy and $C_1\text{-}C_4$ acyl and
m is a number from 1 to 10 and in which the conjugates preferably have at least one binding site which, after immobilization of the conjugates on a solid phase, can still bind with high affinity to a soluble reactant.

In a further preferred embodiment, conjugates of the general structural formula (III) are used:

in which
P' is a partner of a high affinity binding pair,
r' is a number from 1 to 10,
F is a biomolecule,
r is a number from 1 to 10 and
AO, n, T and m are defined as for conjugates of structural formula (II).

Conjugates of the structural formulae (II) and (III) are preferably used as a universal or analyte-specific solid phase reactant in detection methods.

The second aspect of the present invention also concerns a solid phase with a coating which contains conjugates of the general structural formula (II) or/and (III). The conjugates can be used to reduce unspecific binding to a solid phase in a method for the determination of an analyte for example in an immunological method or in a nucleic acid hybridization method. The second aspect of the invention additionally concerns a reagent kit for the detection of an analyte which contains a conjugate of the general structural formula (II) or (III) or a solid phase coated with such a conjugate in addition to other test components.

A third aspect of the present invention concerns a method for the detection of an analyte in a sample comprising the steps:
(a) preparing a solid phase on which an analyte-specific solid phase reactant is immobilized,
(b) incubating the sample with the solid phase and a test reagent in which the test reagent contains an analyte-specific modified soluble reactant which is coupled to a poly($C_2$-$C_3$)-alkylene oxide and
(c) detecting the presence or/and the amount of the analyte in the sample.

In this aspect of the invention a modified soluble analyte-specific reactant is used i.e. a biomolecule which can specifically bind to an analyte or/and analyte analogue to be determined. The modified soluble reactant can be directly labelled i.e. carry a labelling group e.g. an enzyme, fluorescent or electrochemiluminescent labelling group. On the other hand the soluble reactant can also be indirectly labelled i.e. it carries a group that can react with a detectable labelling group e.g. a hapten which can in turn react with a labelled anti-hapten antibody.

The modified soluble reactant is preferably selected from antibodies, antigens, nucleic acids, nucleic acid analogues and lectins.

According to this third aspect of the present invention conjugates of the general structural formula (IV) are preferably used:

in which
M is a labelling group or a group that can react with a labelling group,
s is a number from 1 to 10,
F''' is a soluble biomolecule in particular selected from antibodies, antigens, nucleic acids, nucleic acid analogues and lectins and
AO, n, T and m are defined as for conjugates of the structural formula (II).

These conjugates can be used to reduced unspecific binding to a solid phase in a method for the determination of an analyte, in particular in an immunological determination method, a nucleic acid hybridization method or a sugar-lectin determination method. Furthermore this third aspect of the present invention concerns a reagent kit for the detection of an analyte which contains a conjugate of the general formula (IV) in addition to other test components.

A fourth aspect of the present invention concerns a method for reducing unspecific binding to a solid phase in a method for the detection of an analyte in a sample characterized in that at least one reagent is used which contains a substance coupled to a poly($C_2$-$C_3$)-alkylene oxide.

The substance coupled to a poly($C_2$-$C_3$)-alkylene oxide is preferably selected from
(i) blocking substances,
(ii) universal solid phase reactants
(iii) analyte-specific solid phase reactants and
(iv) soluble reactants.

It is preferable to use more than one alkylene oxide modified class of substances in the method.

One subject matter of this fourth aspect of the invention is a reagent kit for the detection of an analyte comprising at least one reagent which contains a substance coupled to a poly($C_2$-$C_3$)-alkylene oxide which is preferably selected from one of the previously mentioned substance classes.

The invention is further elucidated by the following examples.

EXAMPLES

1. Synthesis of a Biotin-polyethylene Glycol(PEG) Conjugate (MW3499)

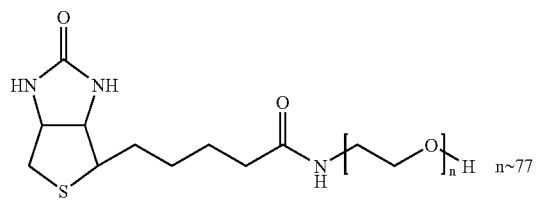

550 mg 1-amino-PEG (Shearwater Polymers Co.) was dissolved in 10 ml dioxane. 60 mg triethylamine was added to this solution and subsequently 100 mg biotin-OSu-ester (Boehringer Mannheim) was added. The mixture was stirred for 2.5 hours at room temperature. Afterwards the product was purified by column chromatography. The yield was 30%.

2. Synthesis of a Biotin-methoxypolyethylene Glycol Conjugate (MW 5000)

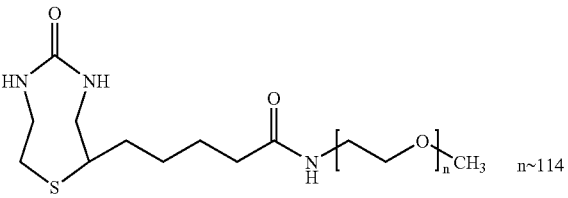

150 mg Aminomethoxy-PEG (Sigma Co.) was dissolved in 100 ml dioxane and subsequently 2 g biotin-OSu ester dissolved in 60 ml DMF was added. After addition of 40 mg triethylamine it was stirred for 3 hours at room temperature and then for a further 3 hours at 70° C. The solvent was subsequently removed and the product was purified by column chromatography. The yield was 57%.

3. Preparation of Biotin-PEG Solid Phase

Biotinylated antibodies to TSH were applied in the form of areas with a diameter of ca. 0.1 mm by means of a microdosing technique to a streptavidin solid phase (p-styrene coated with streptavidin bound to thermally polymerized bovine serum albumin (BSA)). After application of the antibody zones this solid phase was retreated with phosphate buffer pH 7.5 containing 50 µg/ml Bi-PEG. It was rewashed after 2 minutes incubation and dried.

4. Investigation of Unspecific Binding to the Bi-PEG Coated Solid Phase

The solid phase prepared by the method described in example 3 was evaluated with the following system: After incubation with analyte-free sample material (p24-free human serum or Enzymun®-TSH 0 standard) and a subsequent wash step, the solid phases that had been incubated with human serum were incubated with digoxygenilated detection reagent (p24-Dig conjugate and with anti-human IgG-antibody-Dig conjugate). The digoxygenilated reagents are not specific for the anti-TSH antibodies i.e. they do not contain an analyte but represent a marker for the level of unspecific binding. After a wash step, the unspecific binding was determined by a fluorescent dyed latex that was labelled with anti-Dig antibodies. The signals obtained by fluorescent microscopic techniques were quantified by optical image evaluation and stated as counts/sec. The fluorescence intensity within the test areas (containing biotinylated TSH antibodies) and outside the test areas (background without antibody coating) were measured.

TABLE 1

Results in the test area (containing TSH antibodies) in counts/sec

| Solid phase | Detection reagent | | |
|---|---|---|---|
| | TSH 0 standard | p24-Dig | <h-IgG>-Dig |
| without Bi-PEG | 65 | 1897 | 1612 |
| with Bi-PEG | 31 | 740 | 1231 |

TABLE 2

Results in the background (streptavidin solid phase) in counts/sec

| Solid phase | Detection reagent | | |
|---|---|---|---|
| | TSH 0 standard | p24-Dig | <h-IgG>-Dig |
| without Bi-PEG | 51 | 766 | 654 |
| with Bi-PEG | 17 | 136 | 140 |

In all cases the addition of Bi-PEG led to a considerable reduction of unspecific binding on the solid phase.

5. Synthesis of a Streptavidin-polyethylene Glycol Conjugate

Streptavidin and PEG-OSu were dissolved in phosphate buffer and added together in the stoichiometry desired in each case, preferably 1:1 to 1:5. After 2 h reaction at room temperature (?), the reaction mixture was dialysed against phosphate buffer containing 0.05% sodium azide and stored at 4° C.

6. Preparation of a Universal streptavidin-PEG Solid Phase

A reaction vessel was filled with a solution which contained biotinylated carrier protein (BSA-biotin or thermo-BSA-biotin) at a concentration of 100 µg/ml and incubated for 5 min at room temperature. Then the solution was aspirated and the coated reaction vessel was rinsed with phosphate buffer and again aspirated.

Subsequently streptavidin-PEG was added at a concentration of 50 µg/ml in phosphate buffer containing 1% BSA and incubated for 15 min. Afterwards the solution was aspirated and washed by adding phosphate buffer containing 1% BSA and 2% sucrose. After again aspirating and drying, the solid phase was stored at 4° C. in air-tight packaging.

7. Preparation of Specific Streptavidin-PEG Solid Phase

A reaction vessel was filled with a solution which contained biotinylated carrier protein at a concentration of 100 µg/ml and incubated for 5 min. The solution was aspirated, rinsed with phosphate buffer and again aspirated. Then streptavidin-PEG (50 µg/ml) in phosphate buffer containing 1% BSA was added and it was incubated for 15 min. The solution was aspirated, rinsed with phosphate buffer and again aspirated.

Then a biotinylated antibody e.g. a monoclonal anti-TSH-antibody Fab'$_2$ fragment (5 µg/ml) was added and incubated for 15 min. The solution was aspirated and rinsed by adding phosphate buffer containing 1% BSA and 2% sucrose and again aspirated. After drying, the solid phase was stored at 4° C. in air-tight packaging.

8.1 Evaluation of Streptavidin-PEG Solid Phases

A reaction vessel containing the solid phase from example 6 or 7 was incubated for 20 min at room temperature with a prediluted analyte-free sample (horse serum diluted 1:1 with loading buffer 50 mM Tris/HCl pH 7.5, 0.5% BSA, 0.05% Tween 20, 0.9% NaCl). After washing, it was incubated for 20 min in the presence of signal antibody (1 µg/ml monoclonal anti-TSH-antibody IgG-digoxigenin conjugate in loading buffer) and washed again.

After addition of the detection reagent (0.01% solution of fluoro beads coated with monoclonal anti-digoxigenin antibody IgG) it was incubated for 20 min, washed and the fluorescence signal was measured.

TABLE 3

Fluorescence blank values (arbitrary units) on various solid phases

| | unspecific solid phase | specific solid phase |
|---|---|---|
| SA underivatized | 199 | 373 |
| SA-PEG (1:1) | 114 | 114 |
| SA-PEG (1:5) | (100) | (100) |

8.2 Unspecific Binding of Buffer Components

A reaction vessel containing the solid phase from example 6 or 7 was filled with a horse serum sample as described in example 8.2 and washed. Then 0.2 µg/ml p24-digoxigenin in loading buffer was added, incubated for 20 min and it was washed. Then the detection reagent (cf. 8.1) was added, incubated again for 20 min, washed and the fluorescence signal was measured. The results are shown in table. 4.

TABLE 4

Unspecific binding of p24-digoxigenin
(arbitrary units) on various solid phases

|  | unspecific solid phase | specific solid phase |
|---|---|---|
| SA underivatized | 691 | (>1500) |
| SA-PEG (1:1) | 260 | 660 |
| SA-PEG (1:5) | 124 | 365 |

8.3 Unspecific Binding of Human IgG Antibodies

A reaction vessel containing the solid phases prepared in examples 6 and 7 was filled with a sample as described in example 8.1 and washed. The sample was human serum, diluted 1:19 with loading buffer.

Then 1.0 µg/ml monoclonal anti-human IgG-antibody-digoxigenin conjugate in loading buffer was added and it was washed. Subsequently the detection reagent was added, incubated for 20 min, washed again and the fluorescence signal was measured. The results are shown in the following table 5.

TABLE 5

Unspecific binding of human antibodies
(arbitrary units) on various solid phases

|  | unspecific solid phase | specific solid phase |
|---|---|---|
| SA underivatized | 2549 | (>3000) |
| SA-PEG (1:1) | 944 | 1749 |
| SA-PEG (1:5) | 515 | 834 |

9. Preparation of Antibody-PEG Conjugates

PEG-antibody conjugates were prepared as described in example 5 except that a biotinylated antibody was used instead of streptavidin.

10. Preparation of Solid Phases Coated with PEG-Antibody Conjugates

A reaction vessel was incubated for 5 min with a solution which contained 100 µg/ml biotinylated carrier protein (BSA-biotin or tBSA-biotin). Then the solution was aspirated, rinsed with phosphate buffer and aspirated again.

Subsequently 50 µg/ml streptavidin in phosphate buffer containing 1% BSA was added and it was incubated for 15 min. This solution was aspirated, rinsed with phosphate buffer and again aspirated. Afterwards 5 µg/ml biotinylated IgG antibody e.g. a monoclonal anti-TSH-Fab'$_2$ antibody fragment was added and it was incubated for 15 min. The solution was aspirated and a rinsing step with phosphate buffer, 1% BSA, 2% sucrose was carried out. After again aspirating, the reaction vessel was dried and stored at 4° C. in air-tight packaging.

11. Evaluation

11.1 Blank Value

The blank value of the solid phase prepared in example 10 was determined as described in example 8.1. The results are shown in table 6.

TABLE 6

Fluorescence blank values (arbitrary units)
on various solid phases

|  | Signals (arbitrary units) |
|---|---|
| AB underivatized | 270 |
| AB-PEG (1:1) | 94 |
| AB-PEG (1:5) | 57 |

11.2. Unspecific Binding of Buffer Components

The unspecific binding of buffer components to the solid phase prepared in example 10 was determined as described in example 8.2. The results are shown in table 7.

TABLE 7

Unspecific binding of p24-digoxigenin
(arbitrary units) on various solid phases

|  | Specific solid phase |
|---|---|
| AB underivatized | 26658 |
| AB-PEG (1:1) | 23519 |
| AB-PEG (1:5) | 7998 |

11.3. Determination of the Unspecific Binding of Human Antibodies (IgG)

The determination of the unspecific binding of human IgG antibodies to the solid phase prepared in example 10 was carried out as described in example 8.3. The results are shown in Table 8.

TABLE 8

Unspecific binding of human antibodies
(arbitrary units) on various solid phases

|  | Specific solid phase |
|---|---|
| AB underivatized | 11379 |
| AB-PEG (1:1) | 10475 |
| AB-PEG (1:5) | 4446 |

Example 12

Procedure for a <HIV I> Test and Test Results with Negative Samples

An antigen which represents the gp41 of the HIV I virus was applied to a test area of ca. 100 µm diameter on a polystyrene support. 30 µl sample that had been prediluted with sample buffer was pipetted onto the test area and incubated for 20 minutes at room temperature while shaking. After aspirating the sample and washing the test zone with wash buffer, 30 µl reagent solution containing a Dig-labelled gp41 which represents the HIV I antigen was added by pipette and it was again incubated for 20 minutes at room temperature while shaking. After aspirating the reagent solution and washing the test zone with wash buffer, 30 µl detection reagent was pipetted onto the test zone. Fluorescence-dyed latex particles of 100 nm size serve as the detection reagent which are covalently coated with an anti-Dig antibody.

This detection reagent was in turn incubated for 20 minutes at room temperature while shaking, subsequently aspirated, washed and sucked dry. The test zone was irradiated with a HeNe laser at 633 nm wavelength and the fluorescence at 670 nm wavelength was measured with a CCD camera.

The following test-specific reagents were used:

Solid phase antigen: polyhapten composed of gp41 peptide detection antigen: polyhapten composed of gp41-peptide, labelled with Dig.

The following measured values (counts) were measured:

| Sample | background* [counts] | signal test zone [counts] | Signal test zone background | cut-off index** |
|---|---|---|---|---|
| negative control | 148 | 148 | 0 | 0.0 |
| positive sample 1 | 178 | 26435 | 26257 | 88.1 |
| positive sample 2 | 172 | 22908 | 22376 | 76.8 |
| negative sample 1 | 101 | 101 | 0 | 0.0 |
| negative sample 2 | 103 | 103 | 0 | 0.0 |
| negative sample 3 | 93 | 93 | 0 | 0.0 |
| negative sample 4 | 98 | 98 | 0 | 0.0 |
| negative sample 5 (S441) | 86 | 4401 | 4315 | 14.6 |
| negative sample 6 (S480) | 137 | 2690 | 2553 | 8.6 |
| negative sample 7 (S486) | 107 | 3833 | 3726 | 12.6 |
| negative sample 8 (S520) | 116 | 4331 | 4215 | 14.2 |

*the background corresponds to the signal adjoining the test zones
**the cut-off index = $signal_{sample} - signal_{background}/2 \times signal_{negative\ control}$
cut-off index <1 = negative The above table represents an extract from a specificity study. Ca. 240 <HIV I> negative samples were measured in this study. Most of the samples (e.g. negative samples 1-4) exhibited no reaction on the test zones and were therefore unequivocally negative. However, four samples (negative samples 5-8) were found which exhibited a strong unspecific reaction on the test zones and were thus detected as false positive.

Example 13

Improvement of the Specificity by a PEG-derivatized Solid Phase Antigen

In this experiment a <HIV I> test was carried out analogously to example 12. In contrast thereto, an identical antigen which was derivatized with PEG 500 in a stoichiometry ratio of 1:1 was additionally applied to the identical test support next to the HIV I antigen.

The following measured values were obtained:

| | background* | polyhapten-gp41-peptide | | polyhapten-gp41-peptide-PEG | |
|---|---|---|---|---|---|
| Sample | [counts] | Counts** | COI*** | Counts** | COI*** |
| negative control | 52 | 0 | 0.0 | 31 | 0.3 |
| positive control | 63 | 286 | 2.0 | 8383 | 80 |
| positive sample 1 | 212 | 11752 | 111 | 6227 | 57.8 |
| positive sample 2 | 84 | 1632 | 14.9 | 3762 | 35.3 |
| S441 | 50 | 1061 | 9.7 | 79 | 0.3 |
| S480 | 53 | 871 | 7.9 | 102 | 0.5 |

-continued

| | background* | polyhapten-gp41-peptide | | polyhapten-gp41-peptide-PEG | |
|---|---|---|---|---|---|
| Sample | [counts] | Counts** | COI*** | Counts** | COI*** |
| S486 | 44 | 1041 | 9.6 | 98 | 0.5 |
| S520 | 44 | 1260 | 11.7 | 84 | 0.4 |

*the background corresponds to the signal adjoining the test zones
**$signal_{sample} - signal_{background}$
***COI = cut-off index = $signal_{sample} - signal_{background}/2 \times signal_{negative\ control}$
cut-off index <10 negative This result shows that the unspecific binding of the interfering samples in the <HIV I> test zone is substantially reduced by using the new PEG-derivatized antigen so that all 4 interfering samples are negative. Surprisingly the PEG-derivatization was even able to lead to a strong increase of the signal of positive samples (see positive control and positive sample 1).

14. Detection of HBs-antigen

A monoclonal antibody to HBs antigen was applied to a test area of ca. 100 μm diameter on a polystyrene support. The same antibody in the form of a PEG conjugate (preparation example 9) was applied to another test area. 30 μl sample prediluted with sample buffer was pipetted onto the test area and incubated for 20 min at room temperature while shaking. After aspirating the sample and washing the test area with wash buffer, 30 μl reagent solution containing digoxigenin-labelled anti-HBsAg antibody was added by pipette and it was again incubated for 20 min at room temperature while shaking. After aspirating the solution and washing the test area with wash buffer, 30 μl detection reagent (example 8.3) was pipetted onto the test area.

The detection was carried out as described in example 8.1.

The following were examined: a positive standard, a negative standard as well as five negative sera which contain no HBsAg but nevertheless yield significant positive signals in the test which were due to analyte-unspecific interactions with the solid phase. Results of these experiments are listed in table 9. It can be clearly seen that the unspecific binding of PEG-derivatized antibodies is very much lower than that of untreated antibodies.

TABLE 9

| | Measured signal | |
|---|---|---|
| Sample | MAB<HBs> | MAB<HBs>PEG |
| pos. standard | 1080 | 960 |
| neg. standard | 1.3 | 1.7 |
| negative serum 1 | 16 | 3.4 |
| negative serum 2 | 28 | 12 |
| negative serum 3 | 15 | 1.3 |
| negative serum 4 | 11.5 | 2 |
| negative serum 5 | 18 | 9 |

The invention claimed is:

1. A method for the detection of an analyte in a sample, comprising the steps:
   (a) preparing a solid phase on which a preformed conjugate of a poly($C_2$-$C_3$)-alkylene oxide and an analyte-specific reactant that interacts with the analyte has been applied such that the preformed conjugate is immobilized in a test area on the solid phase,
   (b) incubating the sample with the solid phase and a detection reagent that provides a detectable indication of the presence or/and amount of the analyte, such that any analyte in the sample binds to the reactant bound to the solid phase and (c) detecting the presence or/and the amount of the analyte in the sample with the detectable indication, wherein the solid phase is coated with a first member of a high affinity binding pair and said preformed conjugate is immobilized via said high affinity binding pair, wherein said analyte specific reactant in said preformed conjugate is conjugated with a second member of said high affinity binding pair prior to application of said preformed conjugate to said solid phase.

2. The method as claimed in claim 1, wherein said analyte-specific reactant is selected from analyte-specific antibodies, antigens, nucleic acids, nucleic acid analogues and lectins.

3. The method of claim 1 further comprises the step of blocking the solid phase with an analyte-unspecific or inert biomolecules during or after immobilization of said preformed conjugate to said solid phase to reduce unspecific binding.

4. The method for detection of any analyte in a sample, comprising the steps:

(a) forming a conjugate of a poly($C_2$-$C_3$)-alkylene oxide and an analyte-specific reactant that interacts with the analyte, then (b) preparing a solid phase by applying thereto the conjugate of the poly($C_2$-$C_3$)-alkylene oxide and the analyte-specific reactant that interacts with the analyte such that the conjugate is immobilized, (c) incubating the sample with the solid phase and a detection reagent that provides a detectable indication of the presence or/and amount of the analyte, such that any analyte in the sample binds to the reactant bound to the solid phase and (d) detecting the presence or/and the amount of the analyte in the sample with the detectable indication.

5. The method of claim 1, wherein the high affinity binding pair is selected from the group consisting of streptavidin, avidin/biotin, desthiobiotin, iminobiotin, aminobiotin, antidigoxigenin antibody/digoxigenin, and antifluorescein antibody/fluorescein.

6. The method of claim 1, wherein after the solid phase has immobilized thereon the preformed conjugate, said solid phase is further incubated with an alkylene oxide modified analyte-unspecific biomolecule which acts as a blocker.

7. The method of claim 6, wherein the blocker does not bind the analyte.

8. The method of claim 7, wherein the blocker is a protein or polysaccharide.

9. The method of claim 6, wherein the blocker binds to the solid phase by adsorptive or covalent interactions.

10. The method of claim 9, wherein the blocker binds to the solid phase by coupling via high affinity binding pairs.

11. The method of claim 1, wherein the preformed conjugate is immobilized in the presence of an alkylene oxide modified analyte-unspecific. biomolecule which acts as a blocker.

12. The method of claim 1, wherein the solid phase is non-porous.

13. The method of claim 1, wherein said test area is a spatially limited test area.

14. The method of claim 13, wherein the test area is a miniature test area having a diameter of 10 μm to 2 mm.

15. The method of claim 1, wherein the solid phase further comprises additional test areas containing solid phase reactants specific for additional analytes.

* * * * *